(12) United States Patent
Kubanek et al.

(10) Patent No.: US 7,241,445 B2
(45) Date of Patent: Jul. 10, 2007

(54) HUMAN MONOCLONAL ANTIBODY AGAINST HEPATITIS C VIRUS E2 GLYCOPROTEIN

(75) Inventors: Bernhard Kubanek, Ulm (DE); Marcia Da Silva Cardoso, Oberelchingen (DE); Karl Sifmoneit, Dieburg (DE); Shlomo Dagan, Nes-Ziona (IL); Rachel Eren, Netaim (IL)

(73) Assignee: DRK-Blutspendedienst Baden-Wurttemberg, Ulm (DE)

( * ) Notice: Subject to any disclaimer, the term of this patent is extended or adjusted under 35 U.S.C. 154(b) by 189 days.

(21) Appl. No.: 10/343,015

(22) PCT Filed: Jul. 25, 2001

(86) PCT No.: PCT/IL01/00684

§ 371 (c)(1),
(2), (4) Date: Aug. 28, 2003

(87) PCT Pub. No.: WO02/08292

PCT Pub. Date: Jan. 31, 2002

(65) Prior Publication Data

US 2004/0071710 A1    Apr. 15, 2004

(30) Foreign Application Priority Data

Jul. 26, 2000    (IL)    ................. 137522

(51) Int. Cl.
- *A61K 39/42* (2006.01)
- *A61K 39/00* (2006.01)
- *A61K 39/29* (2006.01)

(52) U.S. Cl. ............. 424/149.1; 424/93.1; 530/338.15; 530/387.1; 530/300

(58) Field of Classification Search .............. 530/388.1, 530/388.15, 388.2; 424/93.1, 93.2, 228.1, 424/141.1, 149.1
See application file for complete search history.

(56) References Cited

U.S. PATENT DOCUMENTS

| | | | |
|---|---|---|---|
| 5,849,987 A | 12/1998 | Reisner | |
| 6,692,908 B1 * | 2/2004 | Foung et al. | 435/5 |
| 6,951,646 B1 * | 10/2005 | Reiter et al. | 424/149.1 |

FOREIGN PATENT DOCUMENTS

| | | |
|---|---|---|
| WO | WO 97/40176 A1 | 10/1997 |
| WO | WO 00/05286 A1 | 2/2000 |
| WO | WO 02/057314 A2 | 7/2002 |

OTHER PUBLICATIONS

Illustrated Dictionary of Immunology edited by Dr. Cruse et al. 2nd edition, p. 438, published on 2003, CRC Press.*
Austral Biologicals, CA; based on Choo et al. (1991) PNAS 88:2451.
Choo et al., "Genetic Organization And Diversity Of The Hepatitis C Virus", *Proc. Natl. Acad. Sci. USA*, vol. 88, pp. 2451-2455 (Mar. 1991).
Burioni et al., "Dissection Of Human Humoral Immune Response Against Hepatitis C Virus E2 Glycoprotein By Repertoire Cloning And Generation Of Recombinant Fab Fragments", *Hepatology*, 28:810-814 (Sep. 1998).
Cardoso et al, "Isolation and Characterization of Human Monoclonal Antibodies Against Hepatitis C Virus Envelope Glycoproteins", *Journal of Medical Virology*, vol. 55, No. 1, pp. 28-34 (May 1998).
Cohen, "The Scientific Challenge Of Hepatitis C", *Science* vol. 285:26-30 (Jul. 2, 1999).
Habersetzer et al., "Characterization Of Human Monoclonal Antibodies Specific To The Hepatitis C Virus Glycoprotein E2 With In Vitro Binding Neutralization Properties", *Virology*, 249:32-41 (1998).
Hadlock et al., "Human Monoclonal Antibodies that Inhibit Binding Of Hepatitis C Virus E2 Protein to CD81 and Recognize Conserved Conformational Epitopes", *Journal of Virology*, vol. 74, No. 22, pp. 10407-10416 (Nov. 2000).
Harada et al., "Establishment Of A Cell Line Constitutively Expressing E2 Glycoprotein Of Hepatitis C Virus And Humoral Response Of Hepatitis C Patients To The Expressed Protein", *J. Gen. Virol.*, 76:1223-1231 (1994).
Houghton, "Chapter 32: Hepatitis C viruses", In *Fields Virology: Third Edition*, Fields et al. (eds), Lippincott-Raven, Philadelphia, pp. 1035-1058 (1996).
Kato et al, "Characterization Of Hypervariable Regions In The Putative Envelope Protein Of Hepatitis C Virus", *Bioch. Biophys. Res. Commun.*, vol. 189, No. 1, pp. 119-127 (1992).
Kohler & Milstein, "Continuous Cultures Of Fused Cells Secreting Antibody Of Predefined Specificity", *Nature*, 256:495-497 (1975).
Rosa et al., "A Quantitative Test To Estimate Neutralizing Antibodies To The Hepatitis C Virus: Cytofluorimetric Assessment Of Envelope Glycoprotein 2 Binding To Target Cells", *Proc. Natl. Acad. Sci. USA*, vol. 93:1459-1763 (1996).
Siemoneit et al., "Isolation And Epitope Characterization Of Human Monoclonal Antibodies To Hepatitis C Virus Core Antigen", *Hybridoma*, 13:9-13 (1994).
Zibert et al., "Epitope Mapping Of Antibodies Directed Against Hypervariable Region 1 In Acute Self-Limiting And Chronic Infections Due To Hepatitis C Virus", *J. Virol*, vol. 71, No. 5, pp. 4123-4127 (May 1997).
Zibert et al., "Antibodies In Human Sera Specific To Hypervariable Region 1 Of Hepatitis C Virus Can Block Viral Attachment", *Virology*, 208:653-661 (1995).

* cited by examiner

*Primary Examiner*—Bruce R. Campell
*Assistant Examiner*—Bao Qun Li
(74) *Attorney, Agent, or Firm*—Browdy and Neimark, PLLC (57) ABSTRACT

Disclosed is a hybridoma cell line which produces human antibodies capable of binding to the hepatitis C virus (HCV) E2 glycoprotein and capable of neutralizing HCV infection in vivo in an animal model, as well as antibodies produced by the cell line. Also disclosed are various uses of said antibodies in the prevention and treatment of HCV infection. Peripheral blood lymphocytes obtained from human donors having a high titer of anti HCV E2 antibodies are transformed in vitro by Epstein-Barr virus and then fused with heteromyeloma cells to generate hybridomas secreting human antibodies having a high affinity and specificity to HCV E2 glycoprotein.

11 Claims, 9 Drawing Sheets

LIGHT CHAIN

FW1
GACATCCAGATGACCCAGTCTCCTTCCACCCTGTCTGCATCTATAGGAGACAGAGTCACCATCACTTGC

CDR1
CGGGCCAGTCTGAATATTCTTACCTGGTTGGCC

FW2
TGGTATCAGCAGAAACCAGGAAAGCCCCTAAACTCCTCATCTAT

CDR2
GAGGCATCTAGTTTAGAAAGT

FW3
GGGGTCCCATCAAGGTTCAGCGGCAGTGGATCTGGGACTCAATTCACTCTCACCATCAGCAGCCTGCAGCCTGATGATTTTGCAACTTATTACTGC

CDR3
CAACAGTCTAATACTCCCTGGACG

FW4
TTCGGCCAAGGGACCAAGGTGGAAATCAAACGA

HEAVY CHAIN

FW1
CAGGTGCAGCTGGTGGAGTCTGGGGGAGGCGTGGTCCAGCCTGGGAGGTCCCTGAGACTGTCCTGTGCAACCTCTGGATTCCCCTTCAGT

CDR1
AGCTATGGCATGCAC

FW2
TGGGTCCGCCAGGCTCCAGGCAAGGGCCTGGAGTGGGTGGCA

CDR2
GTTATTCCTATGATGGAAGTAATGAACACTCTATAGACTCTGTGAAGGGC

FW3
CGATTCACCATCTCCAGAGACAACTCCAAGAACAGTTGTATCTGCAAATGAACAGTCTGAGAGCTGAGGACATGGCTGTGTATTTCTGTGTCAGA

CDR3
GGGGCGCATAGGAGCAGTTGGTCAGGAAAGCGCTTTGACTAC

FW4
TGGGGCCAGGGAACCCTGGTCACCGTCTCCTCA

FIG.3

$V_L$ AMINO ACID SEQUENCES

| FW1 | CDR1 | FW2 | CDR2 | FW3 |
|---|---|---|---|---|
| DIQMTQSPSTLSASIGDRVTITC | RASLNILTWLA | WYQQKPGKAPKLLIY | EASSLES | GVPSRFSGSGSGTQFTLTISSLQPDDFATYC |

| CDR3 | FW4 |
|---|---|
| QQSNTPWT | FGQGTKVEIKR |

$V_H$ AMINO ACID SEQUENCES

| FW1 | CDR1 | FW2 | CDR2 | FW3 |
|---|---|---|---|---|
| QVQLVESGGGWQPGRSLRLSCATSGFPFS | SYGMH | WVRQAPGKGLEWVA | VISYDGSNEHSIDSVKG | RFTISRDNSKNRLYLQMKSLRAEDMAVYFCVR |

| CDR3 | FW4 |
|---|---|
| GAHRSSWSGKRFDY | WGQGTLVTVSS |

SEQUENCE LISTING

<160> NUMBER OF SEQ ID NOS: 4

<210> SEQ ID NO 1
<211> LENGTH: 369
<212> TYPE: DNA
<213> ORGANISM: Human

<400> SEQUENCE: 1

```
caggtgcagc tggtggagtc tggggggaggc gtggtccagc ctgggaggtc cctgagactg      60
tcctgtgcaa cctctggatt ccccttcagt agctatggca tgcactgggt ccgccaggct     120
ccaggcaagg gcctggagtg ggtggcagtt atttcctatg atggaagtaa tgaacactct     180
atagactctg tgaagggccg attcaccatc tccagagaca actccaagaa caggttgtat     240
ctgcaaatga agagtctgag agctgaggac atggctgtgt atttctgtgt cagaggggcg     300
cataggagca gttggtcagg aaagcgcttt gactactggg gccagggaac cctggtcacc     360
gtctcctca                                                             369
```

<210> SEQ ID NO 2
<211> LENGTH: 321
<212> TYPE: DNA
<213> ORGANISM: Human

<400> SEQUENCE: 2

```
gacatccaga tgacccagtc tccttccacc ctgtrtgcat ctataggaga cagagtcacc    60
atcacttgcc gggccagtct gaatattctt acctggttgg cctggtatca gcagaaacca   120
gggaaagccc ctaaactcct catctatgag gcatctagtt tagaaagtgg ggtcccatca   180
aggttcagcg gcagtggatc tgggactcaa ttcactctca ccatcagcag cctgcagcct   240
gatgattttg caacttatta ctgccaacag tctaatactc cctggacgtt cggccaaggg   300
accaaggtgg aaatcaaacg a                                              321
```

<210> SEQ ID NO 3
<211> LENGTH: 107
<212> TYPE: PRT
<213> ORGANISM: Human

<400> SEQUENCE: 3

Asp Ile Gln Met Thr Gln Ser Pro Ser Thr Leu Ser Ala Ser Ile Gly
1               5                   10                  15

Asp Arg Val Thr Ile Thr Cys Arg Ala Ser Leu Asn Ile Leu Thr Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Gln Ser Asn Thr Pro Trp Thr
                85                  90                  95

Phe Gly Gln Gly Thr Lys Val Glu Ile Lys Arg
            100                 105

<210> SEQ ID NO 4
<211> LENGTH: 123
<212> TYPE: PRT
<213> ORGANISM: Human

<400> SEQUENCE: 4

Gln Val Gln Leu Val Glu Ser Gly Gly Val Val Gln Pro Gly Arg
1               5                   10                  15

Ser Leu Arg Leu Ser Cys Ala Thr Ser Gly Phe Pro Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Glu His Ser Ile Asp Ser Val
    50                  55                  60

Lys Gly Arg Phe Thr Ile Ser Arg Asp Asn Ser Lys Asn Arg Leu Tyr
65                  70                  75                  80

Leu Gln Met Lys Ser Leu Arg Ala Glu Asp Met Ala Val Tyr Phe Cys
                85                  90                  95

```
                                        -continued
Val Arg Gly Ala His Arg Ser Ser Trp Ser Gly Lys Arg Phe Asp Tyr
            100                 105                 110

Trp Gly Gln Gly Thr Leu Val Thr Val Ser Ser
            115                 120
```

HUMAN MONOCLONAL ANTIBODY AGAINST HEPATITIS C VIRUS E2 GLYCOPROTEIN

FIELD OF THE INVENTION

The present invention concerns a hybridoma cell line producing human antibodies capable of binding to hepatitis C virus envelope glycoprotein, antibodies produced by the cell line and various uses thereof.

BACKGROUND OF THE INVENTION

Hepatitis C virus (HCV) infection is a major worldwide health problem. Approximately 170 million individuals worldwide are infected by HCV and chronically infected patients carry a high risk of developing cirrhosis and hepatocellular carcinoma (Cohen 1999 Science 285:26–30).

Interferon-$\alpha$ either alone or in combination with ribavirin is used for therapy of HCV showing efficacy in between 20% and 40% of patients respectively.

HCV is an enveloped virus the genetic information for which is encoded in a 9.5 kilo bases positive strand RNA genome. A highly conserved noncoding region of 341 base pairs is localized at the 5'-end of this viral genome, which is followed by a long open-reading frame coding for a polyprotein of approximately 3,010 amino acids. Two putative envelope glycoproteins, E1 (gp35) and E2 (gp72) have been identified with 5 or 6 and 11 N-linked glycosylation sites, respectively. A high level of genetic variability is associated with the envelope genes. This is highly accentuates at the 5'-end of the E2 gene, where two hypervariable regions termed HVR1 and HVR2, have been described (Kato et al., 1992 Bioch. Biophys. Res. Commun. 189:119–127).

Studies using HCV E1–E2 proteins expressed in mammalian cells showed that infected individuals have an antibody response to HCV E2 (Harada, et al., 1994 J. Gen. Virol. 76:1223–1231). Recent work proposes the existence of neutralizing antibodies in serum from HCV infected patients (Rosa et al., 1996 PNAS (USA) 93:1759–1763; Zibert et al., 1995 Virology 208:653–661; Zibert et al., 1997 J. Virol. 71: 4123–4127).

Investigators employed surrogate assays to provide insights into virus neutralization since the virus cannot be grown in vitro (Houghton. Hepatitis C viruses. In Fields B N, Knipe D M, Howley P M (eds) Virology. Lippincott-Raven, Philadelphia, pp1035–1053). One surrogate assay, the neutralization of binding (NOB) assay, evaluates the ability of a given antibody or serum to prevent the association of HCV E2 protein with a human T-cell line (Rosa et al., 1996 PNAS (USA) 93:1759–1763).

Habersetzer et al., 1998 Virology 249:3241 describes human monoclonal antibodies capable of inhibiting the interaction of HCV E2 with human cells in vitro. Burioni et al., 1998 Hepatology 28:810–814 report human recombinant Fabs for the HCV E2 protein similarly capable of inhibiting the interaction of HCV with human cells in vitro.

PCT patent application WO 200005266 discloses antibodies comprising at least one complementarity determining region (CDR) of the variable domain of a human antibody that specifically recognize a conformation-dependent epitope of HCV E2 and are capable of precipitating E1/E2 complexes.

PCT patent application WO 9740176 discloses a recombinant human antibody Fab portion capable of binding to HCV E2 obtained using a combinatorial antibody library. The relevance of such antibodies for therapy of HCV infection still needs to be demonstrated.

It is therefore of substantial interest to identify human monoclonal antibodies (Mabs) directed against the E2 glycoprotein that are capable of neutralizing HCV infection in vivo. Such antibodies may constitute a new alternative for the treatment of HCV infections.

Cardoso et al., J. Med. Virol. 55, 28–34 (1998) describes the isolation of human monoclonal antibodies capable of binding to hepatitis C virus envelope glycoproteins. One of the described antibodies (4F7) was further characterized and sequenced and is the subject matter of the present invention.

SUMMARY OF THE INVENTION

In accordance with the present invention, a hybridoma cell line is provided which secretes human antibodies capable of binding to the hepatitis C virus envelope glycoprotein E2 and capable of neutralizing HCV infection in vivo in an animal model. In accordance with the invention, peripheral blood mononuclear cells (PBMC) were obtained from human individuals having anti HCV E1/E2 antibodies. PBMC from the human donor may be obtained either by whole blood donation or by leukophoresis. The human PBMC are then transformed in vitro by Epstein-Barr virus (EBV) (Simoneit at al. 1994 Hybridoma 13:9–13). After transformation the resulting anti HCV producing lymphoblastoid cells are fused in vitro preferably with a human-mouse fusion partner such as a heteromyeloma by techniques well known in the art (e.g. Kohler & Milstein, Nature, 256:495–497, 1975). The generated hybridoma cell lines are either cultured in vitro in a suitable medium wherein the desired monoclonal antibody is recovered from the supernatant or, alternatively the hybridoma cell lines may be injected intraperitoneally into mice and the antibodies harvested from the malignant ascitis or serum of these mice. The supernatants of the hybridoma cell lines are screened by any of the methods known in the art such as enzyme linked immunosorbent assay (ELISA) or radioimmunoassy (RIA) for presence of anti HCV E1/E2 antibodies using HCV E1/E2 as a substrate for antibody binding. The human monoclonal anti HCV E1/E2 antibodies thus produced are further examined in a small animal model of HCV infection for their ability to neutralize the virus or reduce the viral load. Virus neutralization or the reduction in viral load may be measured, for example, by RT-PCR analysis of HCV RNA in the animal's sera or by the number of HCV positive mice.

In accordance with the preferred embodiment of the present invention, a hybridoma cell line which was deposited on May 17, 2000, at the European Collection of Cell Cultures (ECACC, CAMR, Salisbury, Wiltshire, SP4 0JG, UK) under the Accession No. 00051714 is provided. Anti HCV E2 human monoclonal antibodies secreted by the above hybridoma cell line designated herein as "HCV-AB 68" as well as fragments thereof retaining the antigen binding characteristics of the antibodies are also provided. Such fragments may be, for example, Fab or F(ab)$_2$ fragments obtained by digestion of the whole antibody with various enzymes as known and described extensively in the art. The antigen binding characteristics of an antibody are determined by using standard assays such as RIA, ELISA or FACS (Fluorescence activated cell sorter) analysis.

The antibodies of the invention have a relatively high affinity to HCV E2 being in the range of about $10^{-9}$ M and $10^{-11}$ M as determined by a BIAcore 2000 instrument (Pharmacia Biosensor).

The antigen bound by the antibodies defined above also constitutes an aspect of the invention.

Further aspects of the present invention are various prophylactic and therapeutic uses of the HCV-AB 68 monoclonal antibodies. In accordance with this aspect of the invention, pharmaceutical compositions comprising the HCV-AB 68 antibodies may be used for the treatment of chronic hepatitis C patients by administering to such patients a therapeutically effective amount of the antibodies or fragments thereof capable of binding to HCV E2. A therapeutically effective amount being an amount effective in alleviating the symptoms of the HCV infection or reducing the number of circulating viral particles in an individual. Such pharmaceutical compositions may also be used, for example, for passive immunization of newborn babies born to HCV positive mothers, and for passive immunization of liver transplantation patients to prevent possible recurrent HCV infections in such patients. A further aspect of the invention is a pharmaceutical composition comprising a therapeutically effective amount of the antibodies of the invention combined with at least one other anti viral agent as an additional active ingredient. Such agents may include but are not limited to interferons, anti HCV monoclonal antibodies, anti HCV polyclonal antibodies, RNA polymerase inhibitors, protease inhibitors, IRES inhibitors, helicase inhibitors, immunomodulators, antisense compounds and ribozymes.

BRIEF DESCRIPTION OF THE DRAWINGS

Individual lanes contain proteins expressed from different E2 constructs or by using different expression systems:
1 E2 BEVS. A recombinant E2 protein produced in insect cells.
2 E2 BEVS without HVR1 (hyper variable region 1). A recombinant E2 protein lacking 33 amino acids at the 5' end.
3 E2 MCS BEVS. A recombinant E2 protein representing the most common sequences from all 6 genotypes of HCV.
4 E2 MCS BEVS without HVR1. A recombinant E2 protein as in 3 that lacks most of the HVR1 except for 4 amino acids.
5 E2 CHO. A recombinant E2 protein produced in CHO cells.

FIG. 2 demonstrates Immuno Magnetic Separation (IMS) of HCV particles from HCV-infected sera by HCV-AB 68 and a control antibody (HCV-AB17).

Reference will now be made to the following Examples that are provided by way of illustration and are not intended to be limiting to the present invention.

EXAMPLES

Materials and Methods

EBV Transformation and Cell Fusion

Peripheral blood mononuclear cells (PBMC) were obtained from an HCV infected human blood donor. The donor was shown to be positive for HCV in a third-generation ELISA (Ortho Diagnostic Systems, Germany) and also in a supplemental test (RIBA, Ortho or Matrix, Abbott). PBMC from this donor were transformed with Epstein-Barr virus (EBV) (Siemonet K et al. 1994, Hybridoma 13: 9–13). The supernatants of the Lymphoblastoid cells produced by the transformation were screened for anti HCV E1/E2 antibody production. The screening was performed by an ELISA using the envelope proteins E1 and E2 of an HCV genotype 1a virus (H strain). Positive clones were fused with the heteromyeloma cell line K6H6/B5 (Cardoso M S et al. 1998, J Med Virol 55: 28–34). The resulting hybridoma clones were screened as above and the positive ones were cloned three times by limiting dilution and finally expanded for antibody production.

Determination of IgG Subclass:

Human IgG subclass was determined by sandwich ELISA using plates coated with either purified goat F(ab)$_2$ anti-human IgG (Chemicon) (0.25 µg/well) or E2 (produced in-house by a Baculovirus expression system) (0.1 µg/well). Mouse anti-human IgG subclasses (IgG1, IgG2, IgG3, IgG4) (Sigma) were used as second antibodies and purified goat anti-mouse IgG peroxidase-conjugate (Zymed Laboratories) as the detection reagent. One hour after incubation at room temperature and washings, substrate solution 3,3',5, 5'-tetramethyl-benzidine dihydrochloride (TMB) (Sigma) was added. Results were read using an ELISA reader at 450 nm.

Affinity Constant Measurements

The affinity constant (KD) of purified HCV-AB 68 to HCV E2 was determined by the BIAcore 2000 instrument (Pharmacia Biosensor) according to the manufacturer's instructions, using BIAevaluation 3.0 software provided by the manufacturer to determine the dissociation rates.

HCV E2 proteins from two different sources were used: 1) E2 CHO, a commercially available recombinant HCV genotype 1b E2 protein produced in mammalian CHO cells (Austral Biologicals, CA; based on Choo et al. 1991 PNAS 88: 2451). It is a truncated protein, comprising of 331 amino acids and electrophoreses as a band of ~60 kD on Western blots. And 2) E2 BEVS, recombinant HCV genotype 1b E2 protein produced in insect cells using Baculovirus as an expression vector. The protein comprises 279 amino acids and lacks 150 amino acids at the 3' hydrophobic end of E2 (These amino acids were deleted in order to render the protein soluble and enable its expression)

Western Blot Analysis

All protein gels were performed using ready-made 4–12% NuPage Bis-Tris gels (Novex, CA). Protein transfer to nitrocellulose was performed using a Xcell II mini-cell (Novex, CA) according the manufacturer's recommendations.

For native gels, 200 ng of each antigen was mixed with a native sample buffer devoid of reducing agent and incubated for 5 min at 37° C. or 100° C. prior to loading. For reducing gels, identical amounts of antigen were mixed with a native sample buffer containing either β-mercaptoethanol (360 mM) or DTT (50 mM) and processed in an identical manner as for native gels.

Following transfer, blots were incubated overnight in blocking buffer (PBS/Milk/0.04% Tween-20) and thereafter incubated with 0.5 µg/ml HCV-AB 68 for 3 hrs. The blots were washed three times with blocking buffer and then incubated with peroxidase conjugated goat-anti human IgG diluted 1:20,000 in blocking buffer for 60 min. Following 3×5 min washes with PBS/0.04% Tween-20, blots were exposed to X-ray film and developed using enhanced chemiluminescence (ECL).

ELISA:

Microtiter plates (F96 Maxisorp Nunc-Immuno Plate, Nunc, Denmark) were coated with E2-BEVS at 2 µg/ml in PBS, 50 µl/well. Purified HCV-AB 68 serially diluted from 1 µg/ml was added to the wells and incubated O.N. at 4° C. Goat anti-human IgG peroxidase-conjugate (Zymed) diluted 1:20,000 was used as $2^{nd}$ antibody. One hour after incubation at 37° C. and washings, substrate solution 3,3', 5,5'-tetramethyl-benzidine dihydrochloride (TMB, Sigma, St. Louis, Mo) was added. Results were read using an ELISA reader, with a wavelength of 450 nm.

Immunoprecipitation of HCV from Human Infected Sera

To determine the ability of HCV-AB 68 to bind HCV particles, an immuno magnetic separation (IMS) assay has been developed. Viral HCV particles present in sera taken from infected patients are captured by magnetic beads coated with a specific antibody. Following magnetic separation of bound to non-bound fractions, these particles are detected by a specific RT-PCR assay.

2 µg of HCV-AB68 were coated on protein-A magnetic beads (Dynal A.S.) according to manufacturer instructions. HBV-AB 17, a monoclonal antibody raised against HBV served as a negative control. All reactions were performed at room temperature. Antibody coated beads were washed 3 times in 0.1 M Na—P buffer pH=8.1, blocked for 30 minutes in 1% BSA, and washed again in PBS before re-suspension in PBS-0.1% BSA. In parallel, tested serum from an infected individual was pre-treated with protein-A sepharose (Pharmacia) to eliminate serum antibodies. This was achieved by incubating 10 µl serum with 10 µl protein-A sepharose for 30 minutes with shaking, followed by a 5 minutes 5000 RPM centrifugation step. The antibody depleted serum was then incubated with shaking for 2 hours with the antibody coated magnetic beads. PBS containing 0.1% BSA was used to complete the final volume to 200 µl. The bound fraction, magnetically separated from the non-bound fraction, was washed 5 times with 1 ml PBS before final re-suspension in 200 µl PBS.

Evaluation of viral amounts in the bound and non-bound fractions was performed by RT-PCR analysis. Viral RNA was extracted using Tri-Reagent BD (Sigma) according to manufacturer instructions. RT reaction (20 µl final volume) contained 4 µl RT buffer, 1mM dNTP's, 10 mM DTT, 100 U mMLV-RT (Promega), 2.7 U ANV-RT (Promega) and 2.5 pM HCV anti-sense primer ATGRTGCTCGGTCTA (SEQ ID NO:5). Reaction conditions were set to ramping from 37° C. to 42° C., with a 1° C. increment every 20 minutes. Reaction was completed by a 10 minutes incubation step at 94° C. 5 µl of RT reaction was used as a template for a PCR reaction (50 µl final volume). PCR reactions contained 5 µl PCR buffer, 2.5 mM MgCl$_2$, 0.2 mM dNTP's, 0.25 U Taq polymerase (Promega), 0.25 pM sense primer CACTCCAC-CATRGATCACTCCC (SEQ ID NO:6) and anti-sense primer ACTCGCAAGCACCCTATCAGG (SEQ ID NO:7). Thirty three amplification cycles of 1 minute at 94° C., 1 minute at 58° C., 1.5 minute at 72° C. were performed, with a final 5 minute elongation step at 72° C. PCR products were separated on a 2% agarose gel, visualized and quantified following EtBr staining on an EagleEye II device.

Sequence Analysis RNA was isolated from 10×10$^6$ hybridoma cells using RNAsol B (TEL-TEX, Inc.). cDNA was prepared from 10 µg of total RNA with reverse transcriptase (RT) and oligo dT (Promega) according to standard procedures in 50 µl reaction volume. PCR was performed on 1 µl of the RT reaction mixture with the following degenerate primers:

```
5' leader primers:
Heavy chain (V_H):                      (SEQ ID NO:8)
5' GGGAATTCATGGAGTTKGGGCTKAGCTGGRTTTTC 3'

Light chain (V_λ):                      (SEQ ID NO:9)
5'-GGGAATTCATGRCCTGSWCYCCTCTCYTYCTSWYC-3'

Or (V_κ):                               (SEQ ID NO:10)
5'-GGGAATTCATGGACATGRRRDYCCHVGYKCASCTT-3'
```

-continued

```
                                           (SEQ ID NO:11)
The 3' primers correspond to human constant
regions:
V_H  5'-GCGAAGCTTTCATTTACCCRGAGACAGGGAGAG-3'

(SEQ ID NO:12)
V_80 5'-GCGAAGCTTCTATGAACATTCTGTAGGGGCCAC-3'

(SEQ ID NO:13)
V_κ  5'-GCGAAGCTTCTAACACTCTCCCCTGTTGAAGCTC-3'.
```

Commonly used single letter codes were incorporated into the primer sequence:
R=A or G S=C or G W=A or T Y=C or T D=A or G or T H=A or C or T V=A or C or G K=G or T The full-length heavy and light chains' cDNA (the PCR reaction products) were cloned into a mammalian expression plasmid. Multiple independent combinations of heavy and light chain DNAs were transfected into tissue culture cells and the supernatant was taken for antibody specific activity assay. Positive combination of heavy and light chain plasmids i.e. a combination that resulted in antibody activity was sequenced. Sequences were analyzed by comparison to Genbank and by alignment to Kabat sequences (Kabat et al., 1991, Sequences of proteins of immunological interest (5$^{th}$ Ed.) U.S. Dept. of Health Services, National Institutes of Health, Bethesda, Md.).

Example 1

Figure 1:
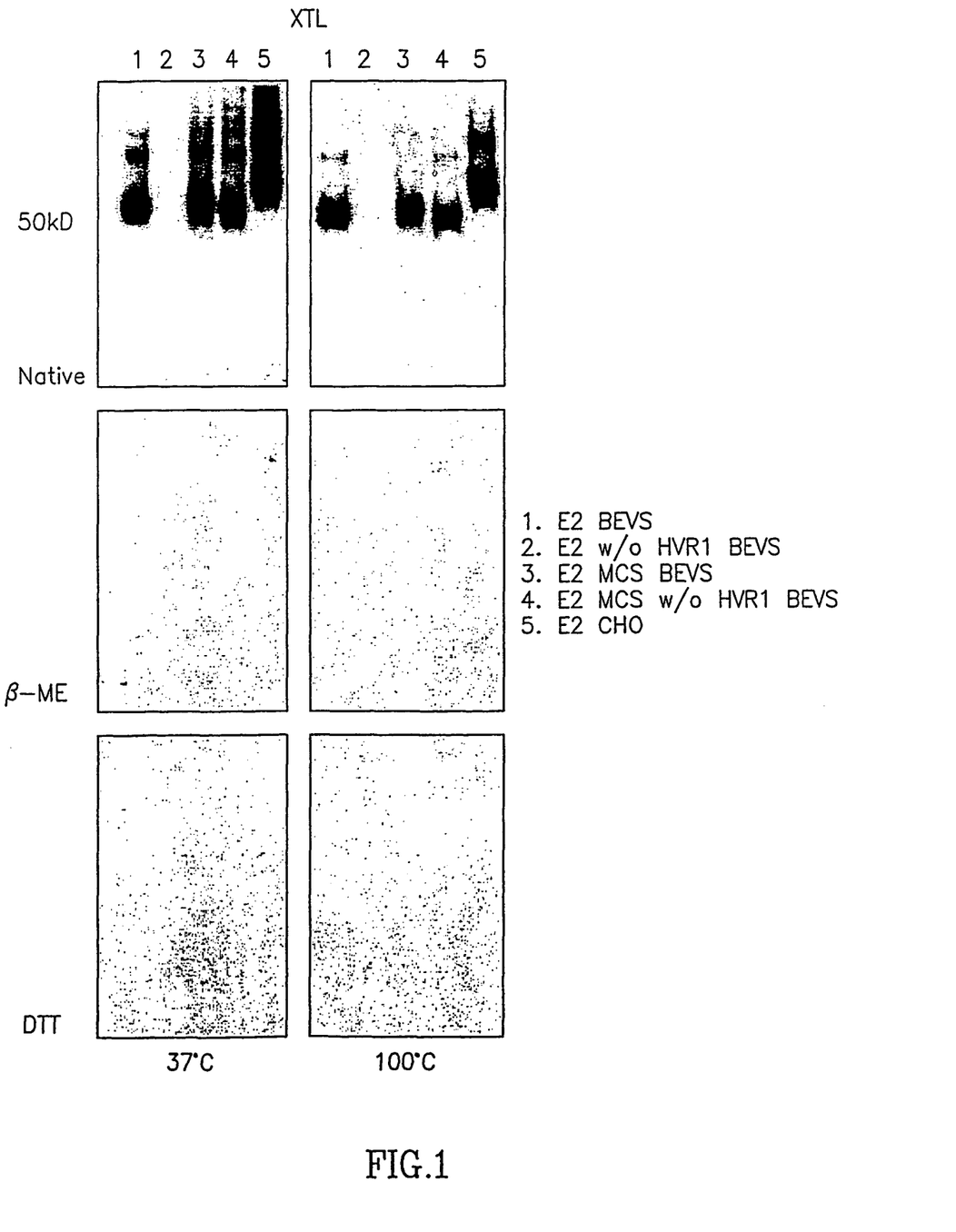
FIG. 1 is a photograph of a Western Blot showing binding of HCV-AB 68 to several E2 proteins treated under various conditions prior to electrophoresis. Panel (a) and (b) represent E2 samples prepared under native conditions. Panel (c) and (d) represent E2 samples treated with β-mercaptoethanol (β-ME). Panel (e) and (f) represent E2 samples treated with DTT. Panel (a) (c) (e) represents E2 samples that were incubated for 5 minutes in 37° C. prior to loading on the gel while in panel (b) (d) (f) samples were heated in 100° C. prior to loading on the gel.

Peripheral blood mononuclear cells (PBMC) from human donors positive for anti HCV antibodies were obtained and transformed in vitro with EBV as described above. The cells were than fused with a human mouse heteromyeloma to form hybridoma cell lines. One of the stable hybridoma clones secreting specific human anti HCV E1/E2 antibodies designated HCV-AB 68 was further characterized. The antibodies secreted by the above clone were found to be IgG1. The affinity constant of HCV-AB 68 to E2 CHO was shown to be $1.4 \times 10^{-11} \pm 0.3$, and to E2 BEVS $1.7 \times 10^{-9} \pm 1$. Specificity was tested by Western Blot analysis and by ELISA. In Western Blot HCV-AB 68 binds different E2 constructs expressed both in a baculovirus expression system (BEVS) and in a mammalian expression system (CHO cells). FIG. 1 demonstrates that HCV-AB 68 binds to all E2 constructs except for construct no. 2, i.e. E2 protein without the HVR1 region. The antibody does not bind to E2 in the presence of β mercaptoethanol or DTT. These results indicate that HCV-AB 68 recognizes a conformational epitope.

Furthermore, the antibody does not bind to construct 2 (which lacks HVR1) but does bind to construct 4 (lacking HVR1 except for 4 amino acids at the 3' end of HVR1, IQLI). It seems that these amino acids form a part of the antibody's binding epitope on E2. Table 1 demonstrates the binding characteristics of HCV-AB 68 to E2 BEVS in ELISA.

TABLE 1

Binding of HCV-AB 68 to E2 by ELISA

| HCV-AB 68 µg/ml | OD$_{450\ nm}$ |
| --- | --- |
| 1 | 0.439 |
| 0.5 | 0.362 |
| 0.25 | 0.305 |
| 0.125 | 0.267 |

TABLE 1-continued

Binding of HCV-AB 68 to E2 by ELISA

| HCV-AB 68 µg/ml | OD$_{450\ nm}$ |
| --- | --- |
| 0.0625 | 0.204 |
| 0.03125 | 0.171 |
| 0.0156 | 0.12 |
| 0.0078 | 0.065 |

Example 2

Figure 2A:
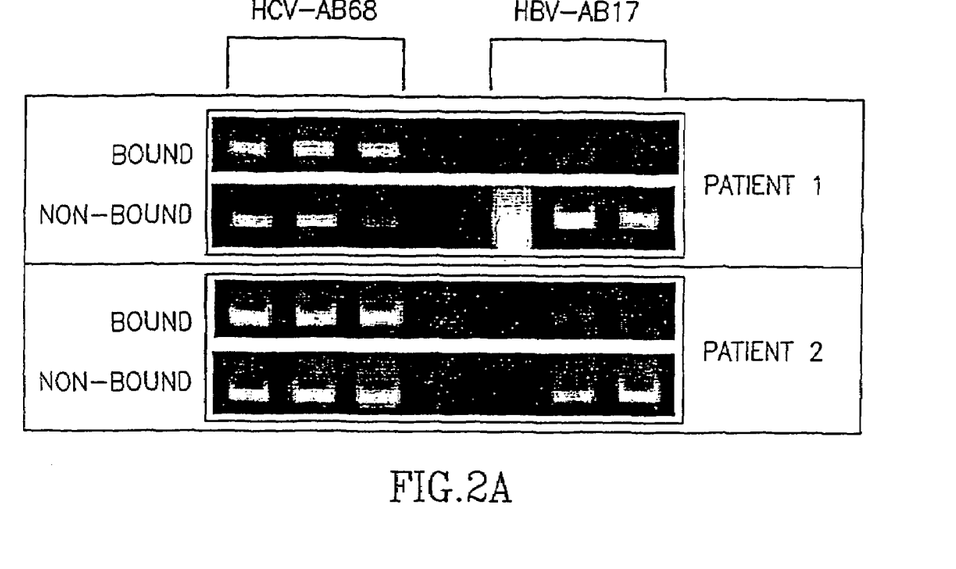
FIG. 2A is a photograph of an agarose gel showing PCR products representing HCV particles.
Figure 2B:
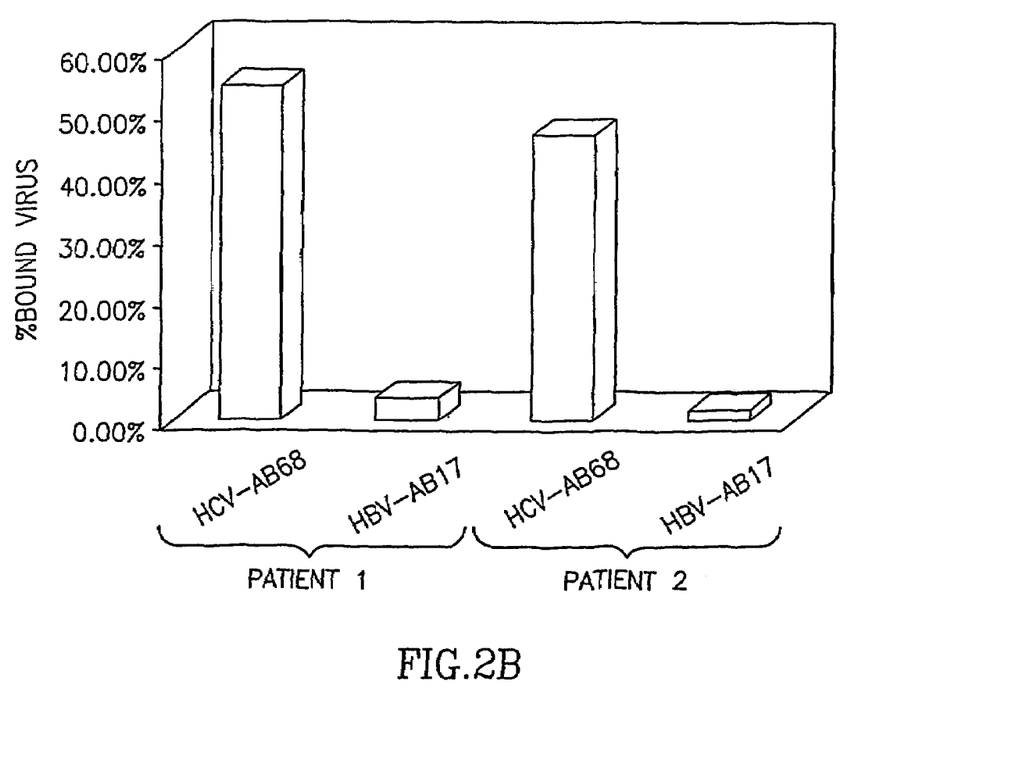
FIG. 2B is a graphic representation of the percentage of bound virus out of the total amount of virus detected by PCR in the bound+unbound fractions.

The HCV-AB 68 antibodies were used to capture HCV particles from the blood of HCV infected patients by immuno magnetic separation (IMS) as described in materials and methods. Two patients were tested in individual experiments where each experiment was performed in triplicate. The HCV genotype of patient 1 is 1b while the genotype of patient 2 is 1a/1b. Each serum has an HCV titer of $1–5 \times 10^6$. FIG. 2 shows that the fraction bound by HCV-AB68 is significantly larger then the fraction bound by the control HBV-AB17. HCV-AB68 can bind more than 50% of the viral particles, while the control HBV-AB17 background binding is between 1–5% (FIG. 2B).

Example 3

Figure 3:
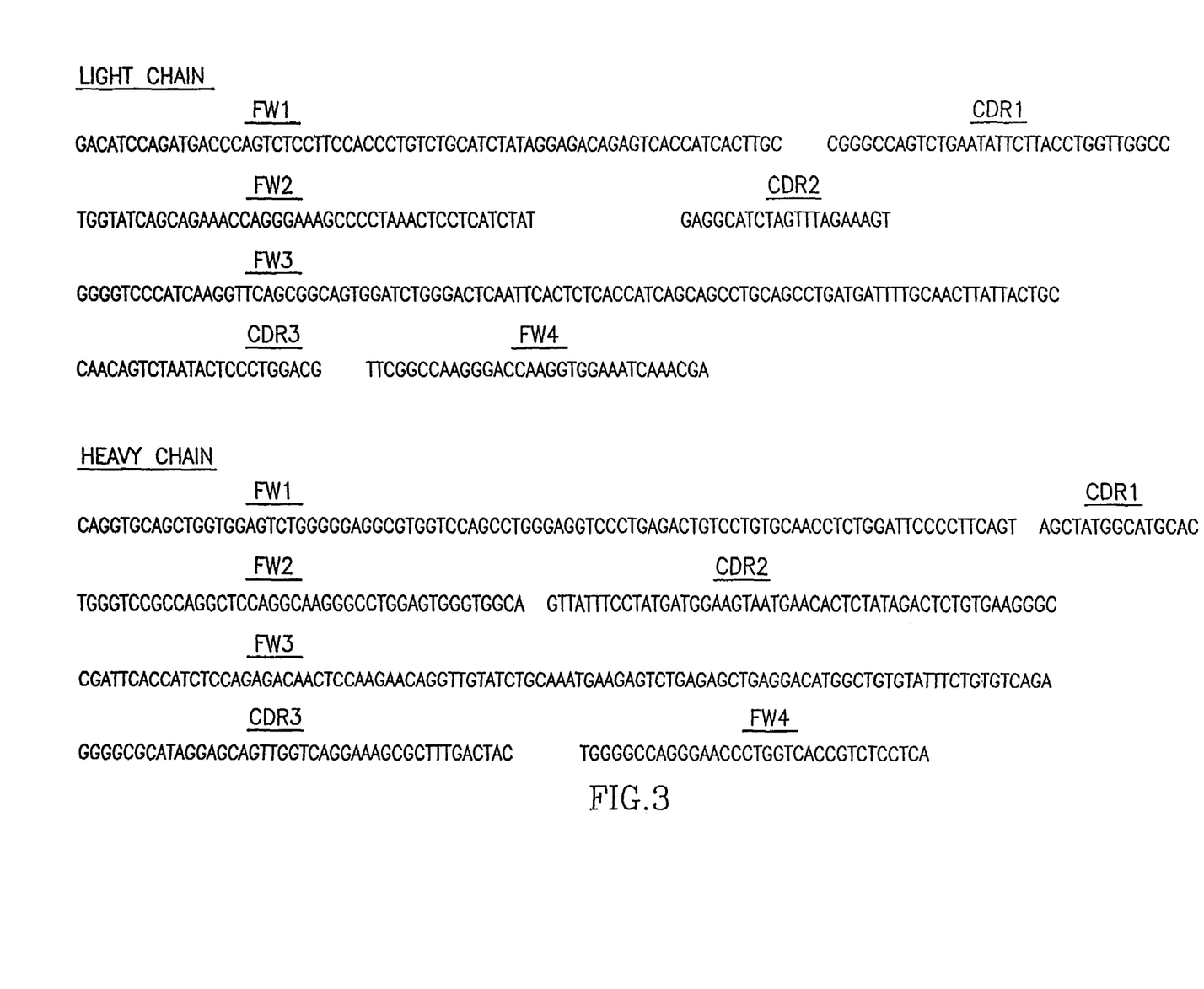
FIG. 3 represents the nucleic acid sequence of the light (SEQ ID NO:2) and heavy (SEQ ID NO:1) chains of the variable domain of HCV-ABG68. The FWs (Frameworks) and CDRs (complementarity determining regions) of the genes are marked.
Figure 4:
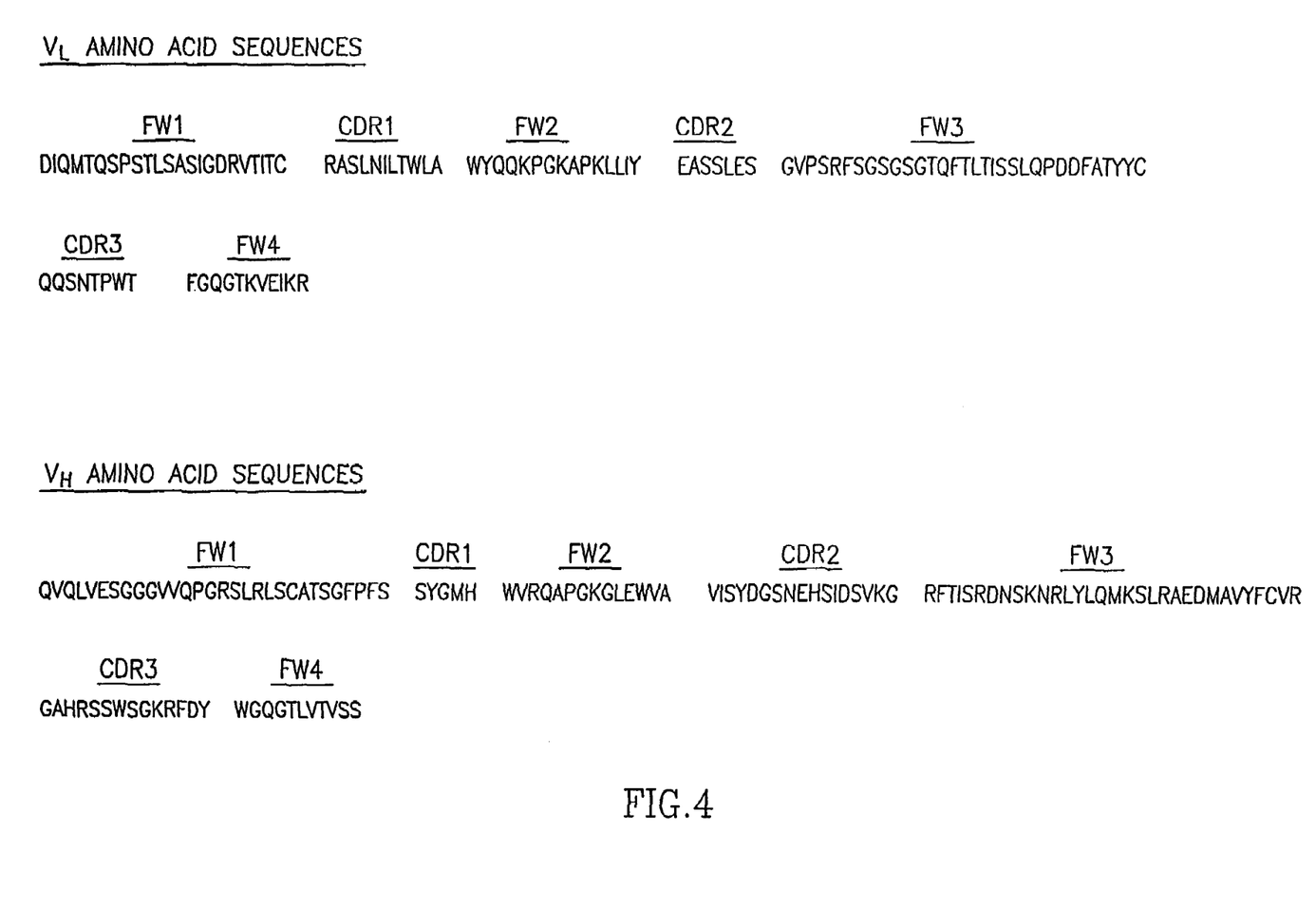
FIG. 4 represents the amino acid sequence of the light ($V_L$) (SEQ ID NO:3) and heavy ($V_H$) (SEQ ID NO:4) chains of the variable domain of HCV-AB 68. The FWs and CDRs of the genes are marked.

The genes encoding the variable regions of HCV-AB 68 were isolated, fully sequenced and subgroups and complementarity determining regions (CDRs) were determined. The antibody has a fully human Ig gene sequence as determined by alignment to Genebank sequences and Kabat protein sequences. FIG. 3 shows the nucleotide sequence of the cDNA encoding the heavy chain and the light chain of the variable region of HCV-AB 68 (Sequence identification numbers 1 and 2 respectively). FIG. 4 shows the corresponding amino acid sequence (Sequence identification numbers 4 and 3 respectively).

The sequencing data revealed that the variable region of HCV-AB 68 consists of the subgroups $V_{H3}\ J_{H4}\ V_{K1}\ J_{K1}$.

Example 4

The biological activity of HCV-AB 68 was characterized using the following HCV-Trimera animal model: a mouse was treated so as to allow the stable engraftment of human liver fragments. The treatment included intensive irradiation followed by transplantation of scid (severe combined immuno deficient) mice bone marrow. Viral infection of human liver fragments was performed ex vivo using HCV positive human serum (U.S. Pat. No. 5,849,987).

The animal model was used in two different modes representing various potential uses of the antibodies: treatment and inhibition of infection.

Figure 5:
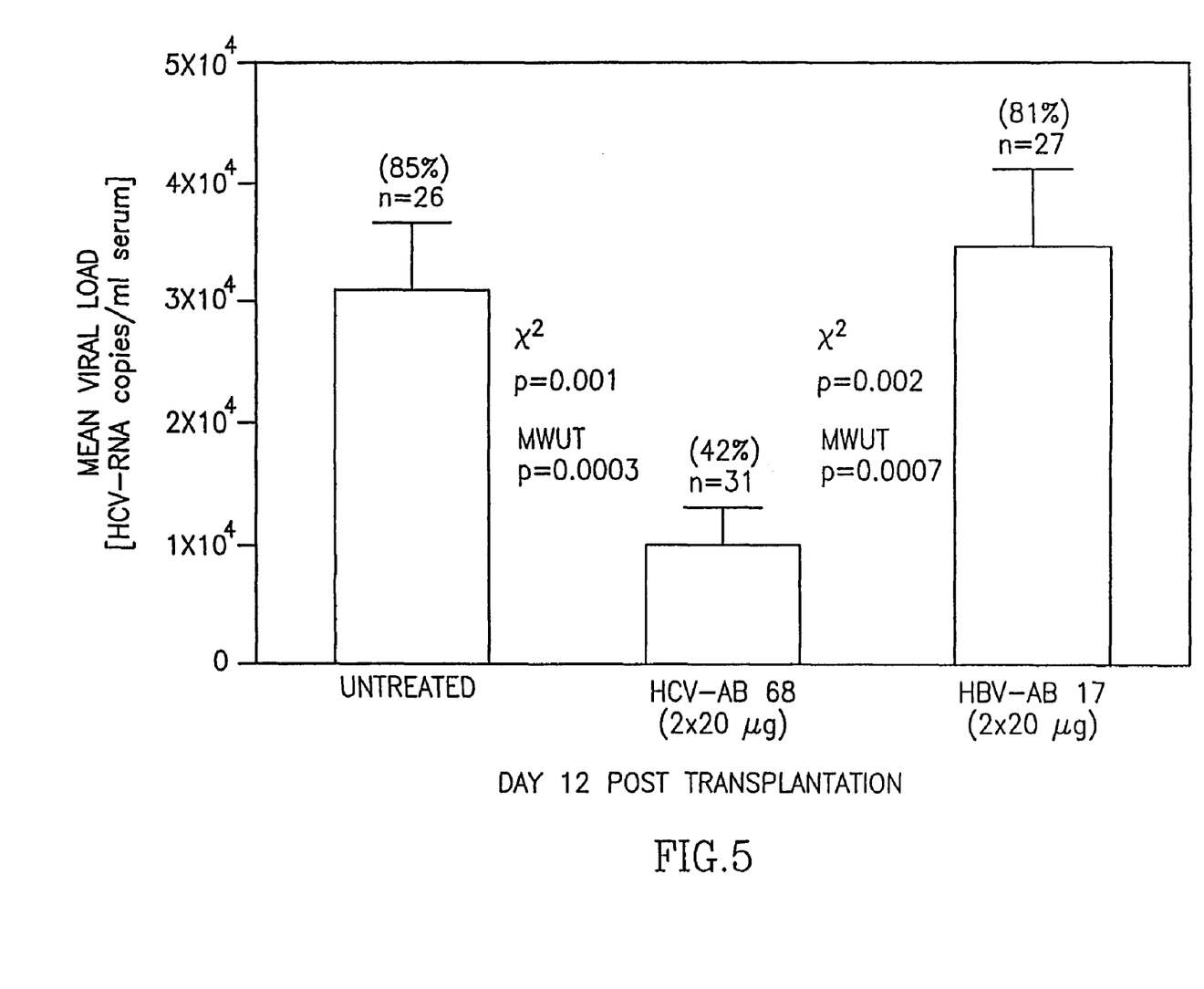
FIG. 5 is a graphic representation of the mean viral load and percentage of HCV infected animals (numbers in parentheses) at day 12 after transplantation in the untreated group, HCV-AB 68 treated group and in a control group treated with HBV-AB 17 (in the treatment mode).
Figure 6:
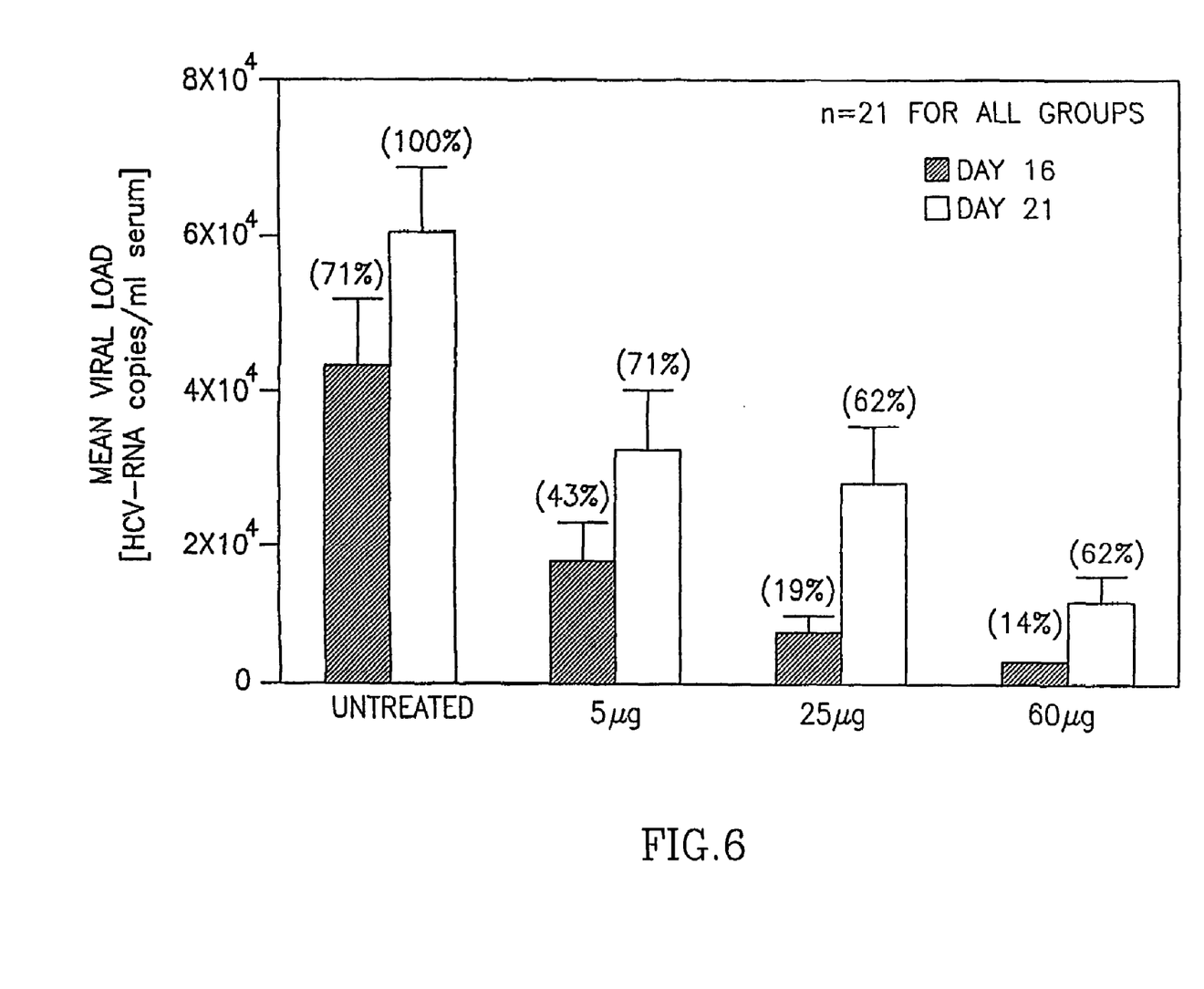
FIG. 6 is a graphic representation of the mean viral load and percentage of HCV-Trimera mice with positive HCV RT-PCR signal in their serum (numbers in parentheses) at days 16 and 21 after transplantation in the untreated group and in the groups treated with different doses of HCV-AB 68.

1. Treatment—This mode demonstrates the ability to use the antibody to treat chronic HCV infection. Trimera mice with established HCV viremia were administered two intraperitoneal injections of HCV-AB 68 or the non-relevant HBV-AB 17; a total of 40 µg mAb per mouse, given at two consecutive days (20 µg/mouse/day). HCV-RNA was determined in mice sera sampled one day after treatment completion. FIG. 5 demonstrates that HCV-AB 68 was able to reduce both the percentage of positive mice (from 85% to 42%) and the mean viral load (from $3.1 \times 10^4$ to 1.0×10⁴ HCV RNA copies/ml). The non-relevant human monoclonal antibody, HBV-AB 17, did not show any ability to reduce the mean viral load or the percentage of positive mice. FIG. 6 shows that the effect of HCV-AB 68 in reducing viral load and percentage of HCV-positive mice is dose dependent. A total dose of 5 µg/mouse reduced the viral load from $4.2×10^4$ to $1.6×10^4$ HCV-RNA copies/ml mouse serum and the percentage of HCV-RNA positive mice from 71% to 43% as measured 1 day post treatment. The highest dose (60 µg/mouse) demonstrated the strongest effect and a reduction in the viral load by more than 1-log factor (from $4.2×10^4$ to $3.1×10^3$ copies/ml) and the percentage of HCV-positive mice from 71% to 14%. Six days after treatment cessation, the viral loads and the percentages of HCV-positive mice, for all 3 doses, bounced somewhat back to levels significantly lower than the levels seen in the untreated control group. At this point in time, a dose response behavior was still observed for the mean viral loads of the different groups.

Figure 7:
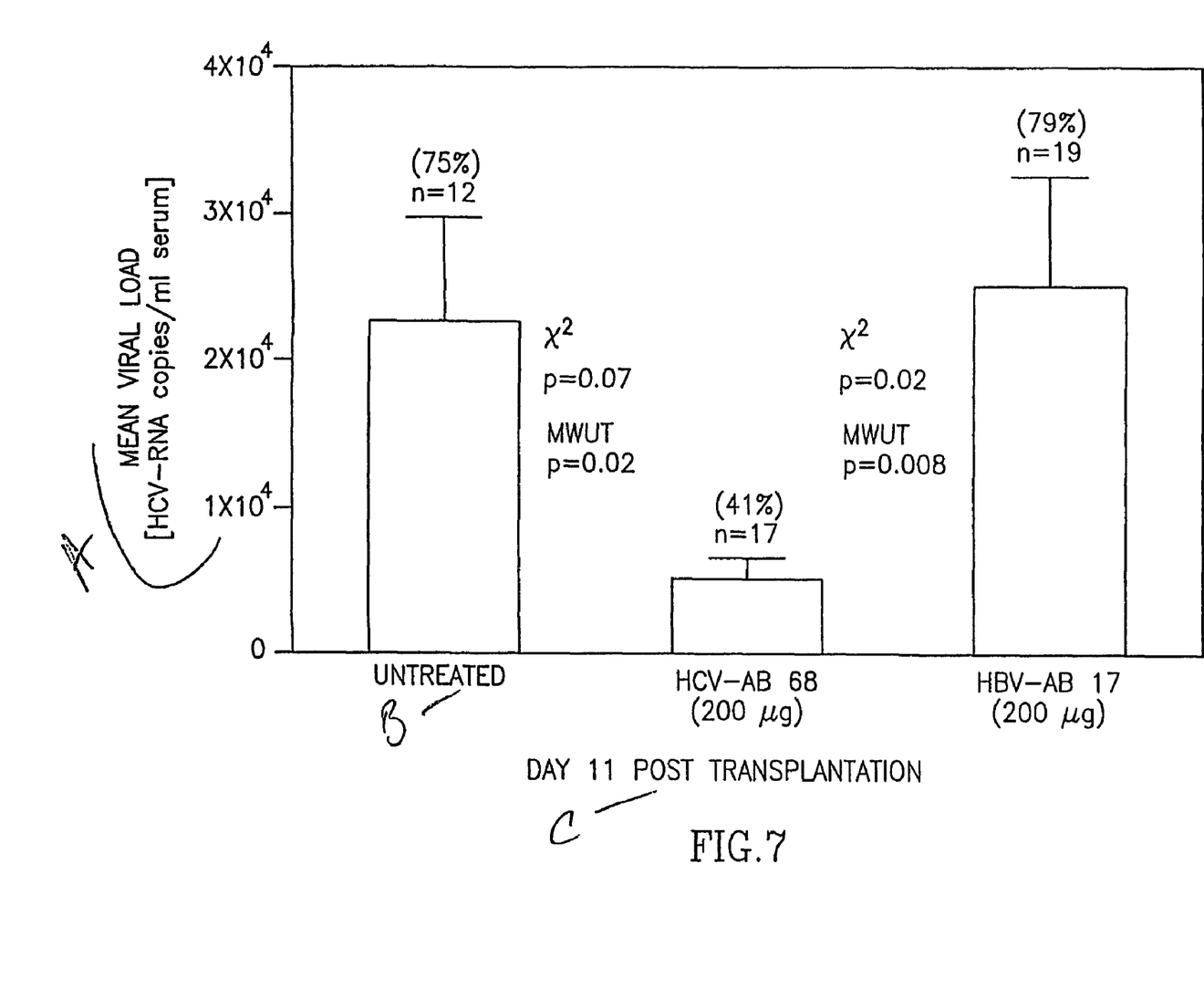
FIG. 7 is a graphic representation of the mean viral load and percentage of HCV-Trimera mice with positive HCV RT-PCR signal in their serum (numbers in parentheses) at day 11 after transplantation in the untreated group, HCV-AB 68 treated group and in a control group treated with HBV-AB 17 (in the inhibition of infection mode).

2. Inhibition of infection—This mode demonstrates the ability to use the antibody to prevent liver infection. 0.5 ml samples of human sera containing $10^6$ HCV-RNA copies/ml were pre-incubated with 200 µg of HCV-AB 68 or with the non-relevant human anti-HBsAg monoclonal antibody HBV-AB 17 (for 3 h at room temperature) and subsequently used to infect normal human liver fragments ex vivo. Following infection, the liver fragments were transplanted in mice and HCV-RNA was determined in sera 11 or 15 days later. FIG. 7 shows the effect of HCV-AB 68 in inhibiting liver infection by HCV, as demonstrated by both the mean viral load and the percentage of HCV-RNA positive mice. HCV-AB 68 reduced the percentage of these mice from 75% to 41%. It also reduced the mean viral load from $2.2×10^4$ to $5.0×10^3$ HCV-RNA copies/ml mouse sera. An equal amount (200 µg) of the non-relevant human monoclonal antibody, HBV-AB17, was not able to reduce neither the percentage of positive mice nor the viral load and gave results that are similar to the untreated control group (FIG. 7). In a different experiment, HCV-AB 68 was able to reduce the percentage of HCV positive mice from 76% to 41% (p=0.05, n=17) and the mean viral load from $6.0×10^4$ to $1.1×10^4$ HCV-RNA copies/ml (p=p.003) as measured in sera that was sampled 15 days post transplantation.

Figure 8A:
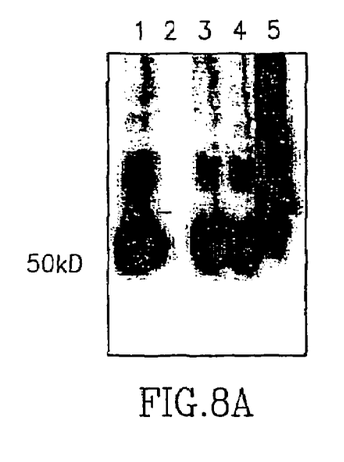
FIG. 8A is a photograph of a Western Blot showing binding of anti HCV antibody 4E5 to several E2 proteins expressed from different E2 constructs or by using different expression systems. Lane numbers correspond to those described in FIG. 1.
Figure 8B:
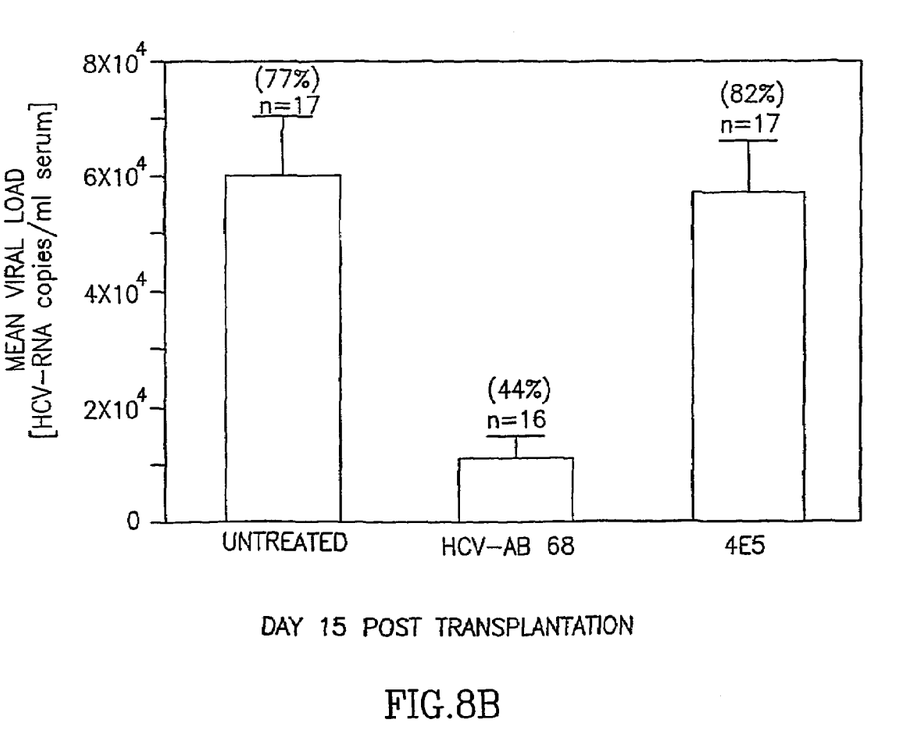
FIG. 8B is a graphic representation of the mean viral load and percentage of HCV-Trimera mice with positive HCV RT-PCR signal in their serum (numbers in parentheses) at day 15 after transplantation in the untreated control group, HCV-AB 68 treated group and in a group treated with 4E5 (in the inhibition of infection mode).

In contrast, another anti HCV human monoclonal antibody 4E5 capable of binding to E2 in vitro as demonstrated by Western blot analysis (FIG. 8A), failed to reduce the percentage of HCV infected mice and the mean viral load in the HCV-Trimera animal model (FIG. 8B).

Example 5

Figure 9:
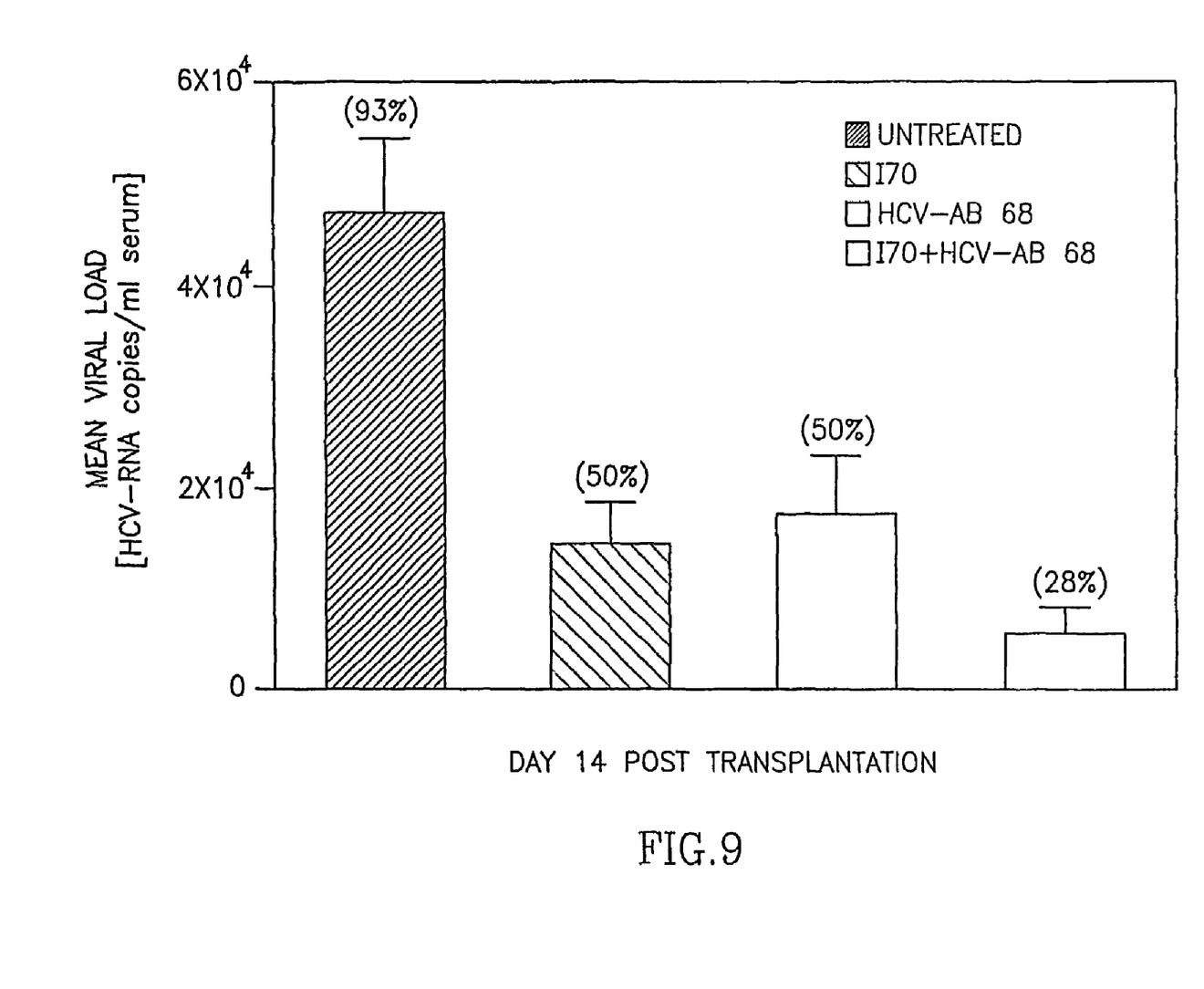
FIG. 9 is a graphic representation of the mean viral load and percentage of HCV-Trimera mice with positive HCV RT-PCR signal in their serum (numbers in parentheses) at day 14 after transplantation in the untreated group, the group treated with I70, the group treated with HCV-AB 68 and the group treated with both I70 and HCV-AB 68.

The therapeutic effects of a combination of two different potential antiviral agents were tested in the HCV-Trimera model. The experiment included four groups of mice. One group was treated with the antiviral drug I70 (obtained from Biochem Therapeutics, a small molecule which inhibits HCV translation). The second group with HCV-AB 68. The third group with a combination of both. And a fourth group served as a control and received only Dulbecco's PBS. In the I70 treatment group each of the mice received 1 mg of the drug at days 10–13 post-liver transplantation (0.25 mg/mouse/day given intraperitoneally (i.p.)). In the HCV-AB 68 treatment group each mouse received 40 µg of the antibody at days 12–13 post-liver transplantation (20 µg/mouse/day i.p.). In the combination group each mouse received a combination of the above treatments. Viral load in mice sera and percentage of HCV-positive mice were determined at day 14 (one day after treatment). FIG. 9 illustrates the therapeutic advantage of using a combination of drugs. Treatment with I70 reduced the HCV mean viral load from $4.72×10^4$ to $1.46×10^4$ and the percentage of HCV-positive mice from 93% to 50%, whereas that with HCV-AB 68 reduced the HCV mean viral load to $1.74×10^4$ and the percentage of HCV-positive mice to 50% as measured 1 day post-treatment. The combination treatment reduced the viral load to $5.83×10^3$ and the percentage of HCV infected animals to 28%.

The invention claimed is:

1. A human monoclonal antibody or fragment, capable of binding to HCV envelope glycoproteins and capable of neutralizing HCV infection in vivo, being selected from the group consisting of:
   (a) a human monoclonal antibody HCV-AB 68, which is secreted by the hybridoma cell line deposited in the European Collection of Cell Cultures (ECACC) under Accession No. 00051714, or a fragment thereof which retains the antigen binding characteristics of HCV-AB68; and
   (b) a human monoclonal antibody or fragment thereof comprising at least a heavy chain variable region whose amino acid sequence is depicted in FIG. 4 (SEQ ID NO: 4) and a light chain variable region whose amino acid sequence is depicted in FIG. 4 (SEQ ID NO: 3).

2. The hybridoma cell line deposited at the ECACC on May 17, 2000 under Accession No. 00051714.

3. A pharmaceutical composition comprising a therapeutically effective amount of the antibody of claim 1 and a pharmaceutically acceptable carrier.

4. A pharmaceutical composition comprising a therapeutically effective amount of the antibody of claim 1 combined with at least one other antiviral agent as an additional active ingredient.

5. A method for the treatment of HCV infections comprising administering to an individual in need thereof a therapeutically effective amount of antibodies according to claim 1.

6. A method for reducing the occurrence of HCV infections in a population of individuals, comprising administering a human monoclonal antibody in accordance with claim 1 to a population of individuals to reduce the occurrence of HCV infections in the population.

7. A method for the treatment of HCV infections comprising administering to an individual in need thereof a therapeutically effective amount of a pharmaceutical composition according to claim 3.

8. A method for the treatment of HCV infections comprising administering to an individual in need thereof a therapeutically effective amount of a pharmaceutical composition according to claim 4.

9. A polypeptide that is the light chain of the variable region of monoclonal antibody HCV-AB 68 having the amino acid sequence illustrated in FIG. 3, or a portion thereof maintaining the HCV binding specificity of monoclonal antibody HCV-AB 68.

10. A polypeptide that is the heavy chain of the variable region of monoclonal antibody HCV-AB 68 having the amino acid sequence illustrated in FIG. 3, or a portion thereof maintaining the HCV binding specificity of monoclonal antibody HCV-AB 68.

11. The pharmaceutical composition of claim 4, wherein said antiviral agent is selected from the group consisting of interferons, anti-HC monoclonal antibodies, anti-HC polyclonal antibodies, RNA polymerase inhibitors, protease inhibitors, IRES inhibitors, helicase inhibitors, antisense compounds and ribozymes.

* * * * *

UNITED STATES PATENT AND TRADEMARK OFFICE
CERTIFICATE OF CORRECTION

PATENT NO. : 7,241,445 B2  Page 1 of 1
APPLICATION NO. : 10/343015
DATED : July 10, 2007
INVENTOR(S) : Kubanek et al.

It is certified that error appears in the above-identified patent and that said Letters Patent is hereby corrected as shown below:

On the cover page, item 75; the last name of the third inventor should read --SIEMONEIT--.

Signed and Sealed this

Thirtieth Day of October, 2007

JON W. DUDAS
*Director of the United States Patent and Trademark Office*